US012458346B2

(12) United States Patent
Reed et al.

(10) Patent No.: US 12,458,346 B2
(45) Date of Patent: Nov. 4, 2025

(54) STAPLE INSTRUMENT

(71) Applicant: Medline Industries, LP, Northfield, IL (US)

(72) Inventors: Wesley Reed, Libertyville, IL (US); Natan Pheil, Highland Park, IL (US); Dinesh Koka, Winter Park, FL (US); Samuel Nader, Arlington Heights, IL (US); Scott Goldstein, Deerfield, FL (US); Ryan Niver, Glenview, IL (US)

(73) Assignee: Medline Industries, LP, Northfield, IL (US)

( * ) Notice: Subject to any disclaimer, the term of this patent is extended or adjusted under 35 U.S.C. 154(b) by 349 days.

(21) Appl. No.: 18/131,141

(22) Filed: Apr. 5, 2023

(65) Prior Publication Data

US 2024/0335193 A1 Oct. 10, 2024

(51) Int. Cl.
*A61B 17/068* (2006.01)

(52) U.S. Cl.
CPC ................................ *A61B 17/0682* (2013.01)

(58) Field of Classification Search
CPC .................................................. A61B 17/0682
See application file for complete search history.

(56) References Cited

U.S. PATENT DOCUMENTS 3,960,147 A 6/1976 Murray
D337,159 S 7/1993 Hunt
5,899,901 A 5/1999 Middleton
6,089,435 A 7/2000 Malek
8,137,351 B2 3/2012 Prandi
9,095,338 B2 8/2015 Taylor
9,855,036 B2 1/2018 Palmer
9,861,413 B2 1/2018 Palmer et al.
9,931,115 B2 * 4/2018 Morgan ............. A61B 17/7291
9,993,246 B1 * 6/2018 Handie .............. A61B 17/0642
10,064,619 B2 9/2018 Palmer
10,130,358 B2 11/2018 Palmer
10,610,218 B2 4/2020 Palmer et al.
10,945,725 B2 3/2021 Hollis
11,284,887 B2 3/2022 Hartdegen
11,426,158 B2 * 8/2022 Palmer ................... A61B 17/10
D977,640 S 2/2023 Ritz
11,596,398 B2 3/2023 Wahl
2016/0199060 A1 * 7/2016 Morgan ............... A61B 17/068
227/175.1
2017/0296174 A1 10/2017 Wahl et al.
(Continued)

FOREIGN PATENT DOCUMENTS

EP 3563776 11/2019

OTHER PUBLICATIONS

Arthrex, Inc. Dynanite Product Technique and Highlights Brochure, 2019.

(Continued)

*Primary Examiner* — Nathaniel C Chukwurah
(74) *Attorney, Agent, or Firm* — Fitch, Even, Tabin & Flannery LLP

(57) ABSTRACT

A staple instrument includes a staple holder comprising a pair of jaws, a drive shaft, a rotational handle, and a coupling to convert rotational motion of the handle into axial advancement of the shaft. A distal end of the shaft cooperates with the staple holder to cause three-point bending of a staple bridge to thereby open the legs of the staple.

7 Claims, 14 Drawing Sheets

(56) References Cited

U.S. PATENT DOCUMENTS

| | | | |
|---|---|---|---|
| 2018/0271521 A1 | 9/2018 | Wahl |
| 2018/0317906 A1 | 11/2018 | Hollis et al. |
| 2018/0344316 A1 | 12/2018 | Palmer |
| 2022/0361877 A1 | 11/2022 | Reed |
| 2023/0027093 A1 | 1/2023 | Wahl |
| 2023/0200809 A1 | 6/2023 | Wahl |

OTHER PUBLICATIONS

CrossRoads® Extremity Systems, LLC Announces Launch of the DynaFORCE™ Dynamic Compression Fixation System, https://www.crextremity.com/crossroads-extremity-systems-llc-announces-launch-of-the-dynaforce-dynamic-compression-fixation-system/, dated Jul. 11, 2017.

DePuy Synthes, BME Elite Implant Technique Overview, 2017.

DePuy Synthes, Speed Memory Implant Brochure, 2016-2018.

MedShape, Inc., Dynaclip Fixation System, Surgical Technique Guide, 2019.

NeoSpan Food, In2Bones, https://web.archive.org/web/20170410093305/http:/i2b-usa.com/neospan-foot/, 2017.

NeoSpan SE Compression Staples, https://i2b-usa.com/neospan-se-compression-staple/, 2021.

Paragon 28, Inc., Surgical Technique Guide: JAWS Nitinol Staple System Brochure, 2020.

Stryker Corporation, "EasyClip Osteosynthesis Compression Staples," 2012.

Stryker Corporation, "EasyClip Osteosynthesis Compression Staples," 2015.

U.S. Food & Drug Administration, 510(k) Premarket Notification, https://www.accessdata.fda.gov/scripts/cdrh/cfdocs/cfpmn/pmn.cfm?ID=K161426, Oct. 24, 2016.

* cited by examiner

STAPLE INSTRUMENT

FIELD

The disclosure relates to medical instruments and, more particularly, to a medical instrument for inserting, removing and adjusting staples into bones.

BACKGROUND

Many surgical procedures take place requiring bone tissue to form between bone segments. The ability for successful bone tissue growth at the site of the bone segments is improved when the bone segments are under compression. If there is no compression, a gap may form between the bone segments. These gaps tend to lengthen the healing time or impede complete healing. One method to achieve compression is the use of compression staples. Compression staples include a pair of legs interconnected by a bridge. These staples are commonly made from material having memory, such as a nitinol alloy, so that when the legs are splayed, they are inclined to return to their natural position.

There is a desire for an instrument that can hold and spread the legs of a compression staple for insertion into drilled holes in adjacent bone segments. There also is a desire for the instrument to be capable of lifting or even removing the staple for repositioning of the staple in the bone segments.

DETAILED DESCRIPTION

Figure 1:
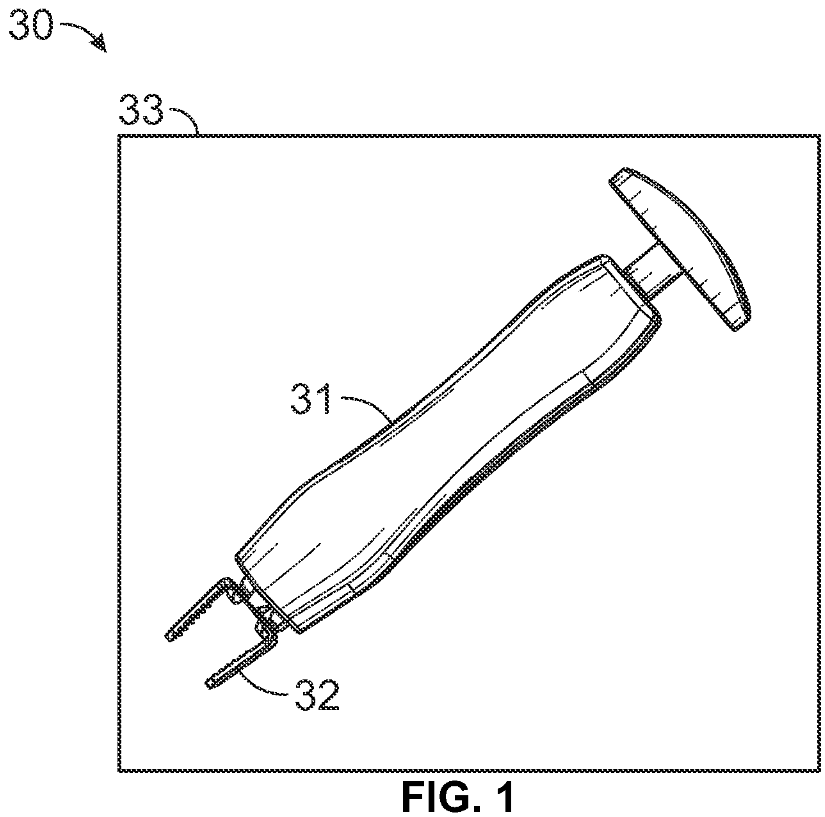
FIG. 1 is a perspective view of a kit that includes a staple instrument and a staple disposed within a container, the staple being loaded on the instrument.

The staple instrument kit 30 shown in FIG. 1 includes a staple instrument 31 and staple 32 within an optional container 33, the container being shown representationally. In practice, the container should be supplied to the operator as a sterilized, sealed package. As supplied, the staple 32 may be loaded onto the staple instrument 31 as shown, or the staple 32 and staple instrument 31 may be supplied as separate components within the container. The kit may include a single instrument and single staple as shown or the kit may include plural staples (not shown). Generally, the staple instrument 31 will be sized to accommodate a particular staple, such that an 18 mm staple would be supplied with a staple instrument sized for an 18 mm staple, a 20 mm staple would be supplied with a correspondingly sized staple instrument, and so on.

Figure 2:
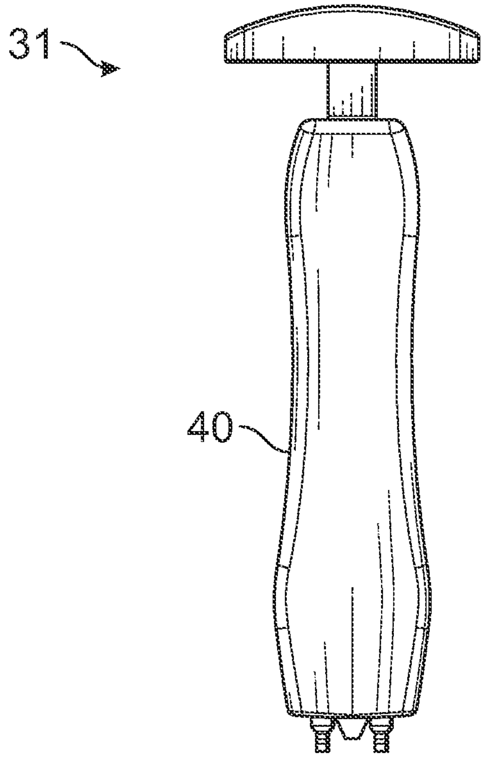
FIG. 2 is a front elevation of the staple instrument of the kit illustrated in FIG. 1.
Figure 3:
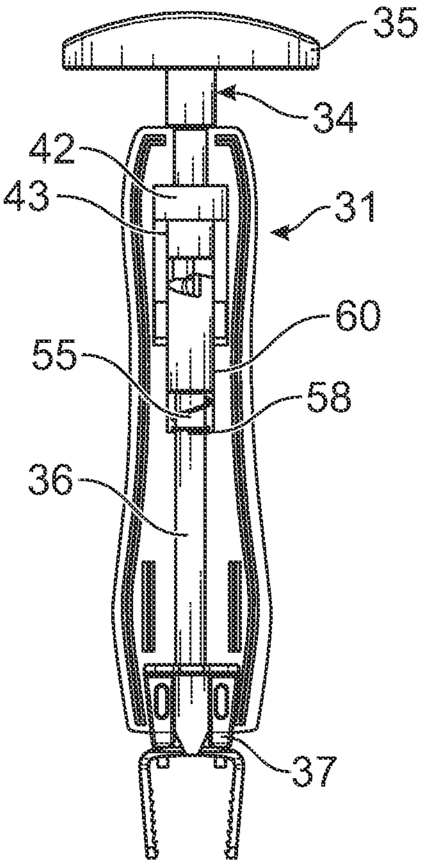
FIG. 3 is a front elevation of the staple instrument shown in FIG. 2 with the front housing portion removed and with a staple loaded.
Figure 4:
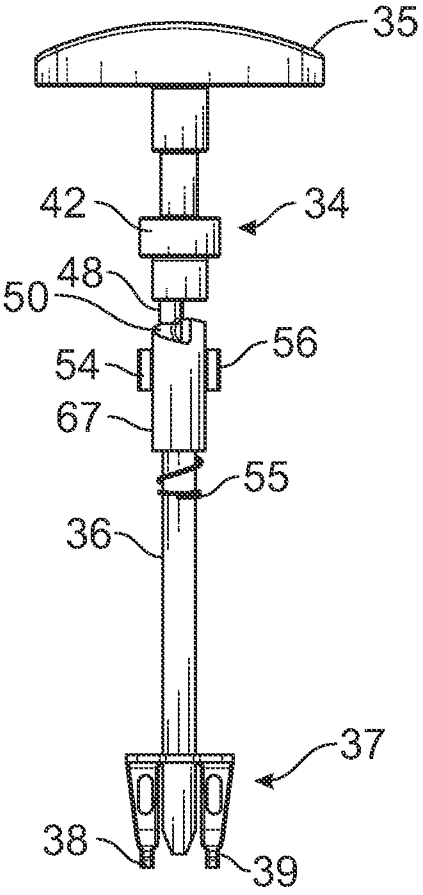
FIG. 4 is a front elevation of components of the staple instrument shown above with the front and rear housing portions removed.

With reference to FIGS. 2-4, the staple instrument includes an operator segment 34 that includes a handle 35, and a shaft 36. The staple instrument 31 also includes a housing 40 (FIG. 2) and a staple holder 37, the staple holder comprising a pair of jaws 38, 39. The housing 40 includes a rear housing portion 41, seen in FIG. 5, and a front housing portion 44, shown in FIG. 6. The front and rear housing portions may be connected to one another via a snap-fit arrangement, or fasteners (not shown) may be used to secure the housing portions together. Slots 47 and 49 (FIGS. 5 and 6 respectively) capture and retain the staple holder 37 when the housing is assembled.

Figure 5:
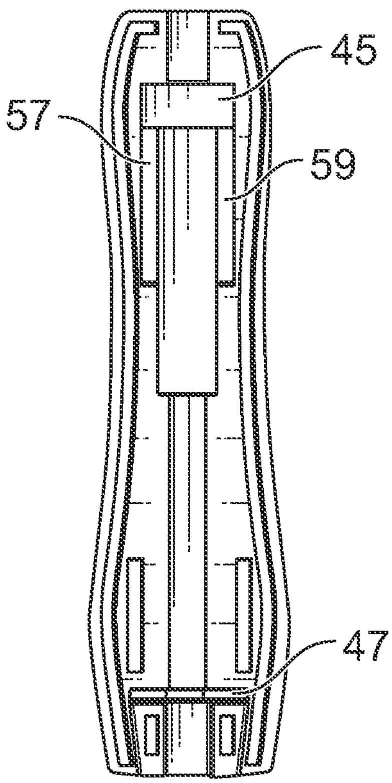
FIG. 5 is a front elevation of the rear housing portion of the staple instrument shown above.
Figure 6:
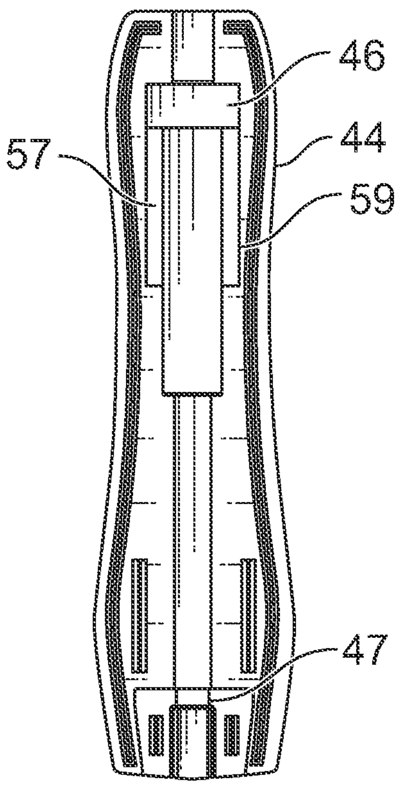
FIG. 6 is a rear elevation of the front housing portion of the staple instrument shown above.
Figure 7:
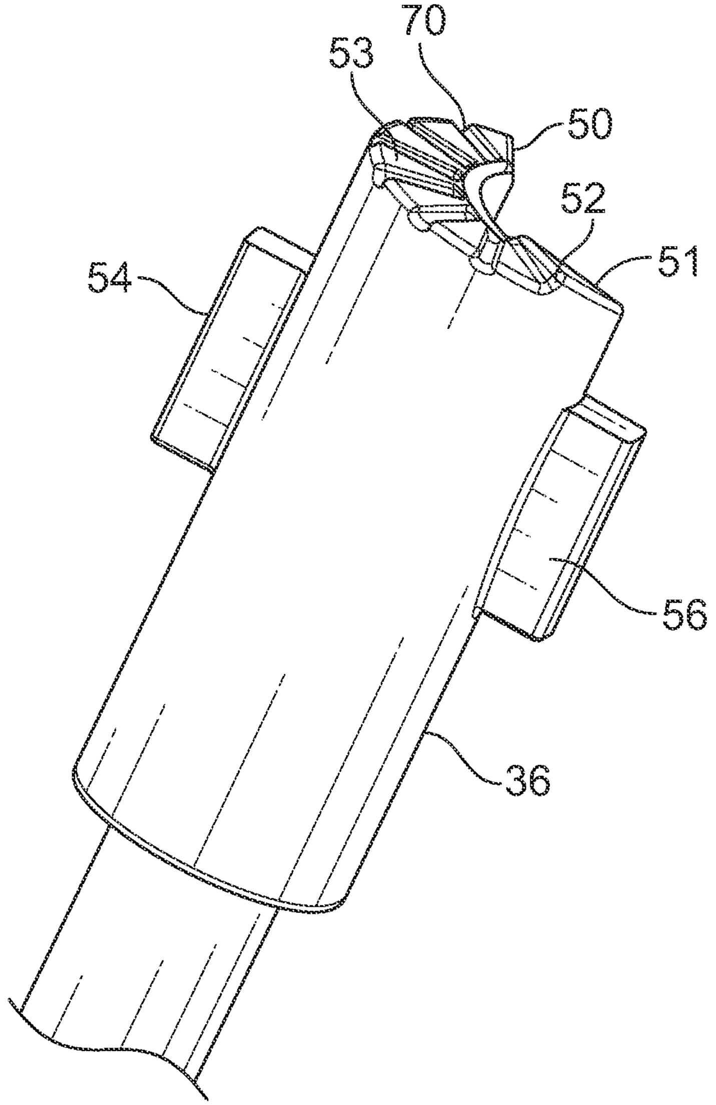
FIG. 7 is a perspective view, relatively enlarged, of the proximal end of the shaft of the staple instrument shown above.
Figure 8:
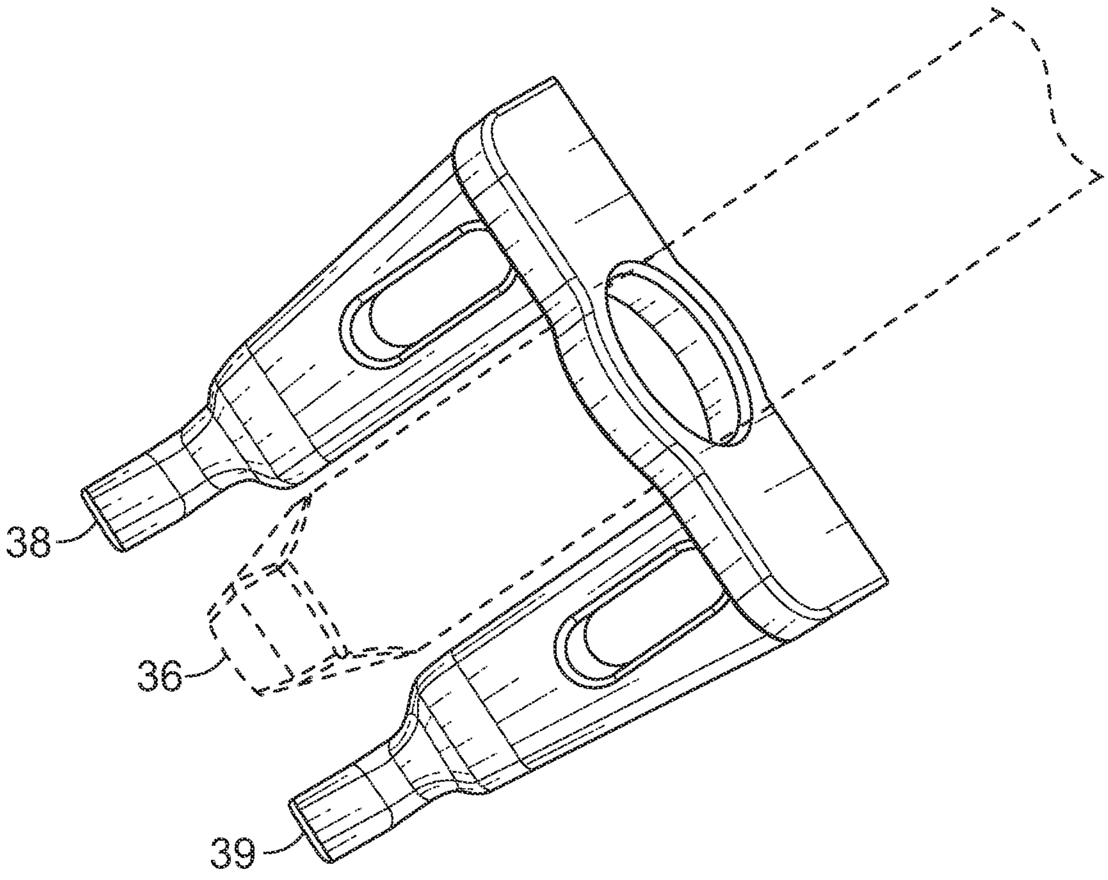
FIG. 8 is a perspective view, relatively enlarged, of the staple holder of the staple instrument shown above, illustrating the shaft of the instrument in phantom lines.
Figure 9:
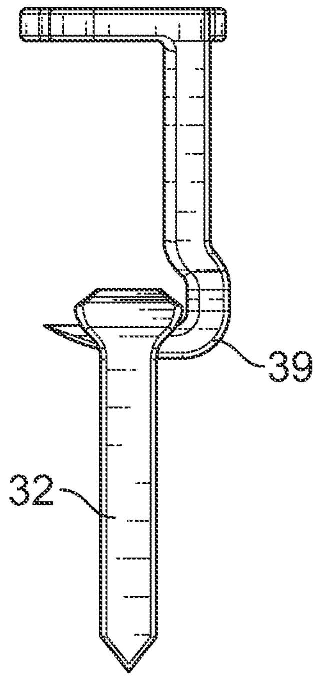
FIG. 9 is a relatively enlarged side elevation of the a portion of distal end of the staple instrument, showing a loaded staple.
Figure 10:
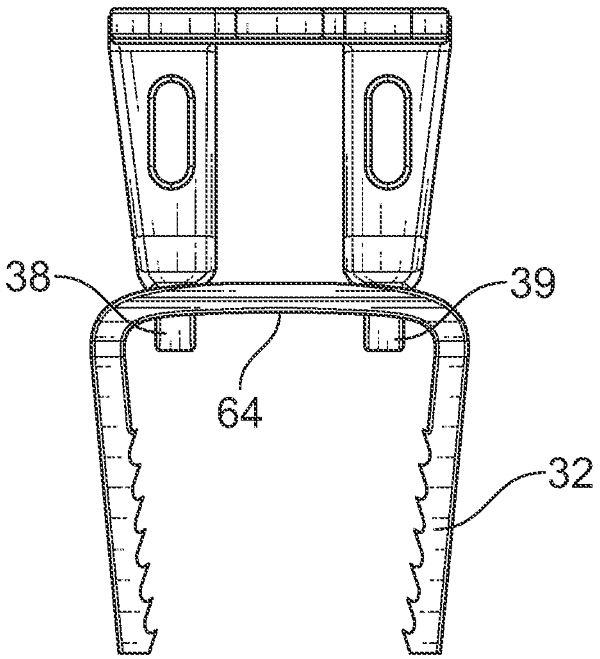
FIG. 10 is a relatively enlarged front elevation of the portion of the distal end of the staple instrument and loaded staple shown in FIG. 9.

Returning to FIGS. 3 and 4, the operator segment 34 has a flange portion 42 that cooperates with a stop 43 (FIG. 3) to retain the operator segment within the housing. The stop is defined in part by cavities 45, 46 as seen in FIGS. 5 and 6 respectively. The distal end of the operator segment 34 includes a cam driver 48, identified in FIG. 4, which cooperates with a cam surface 50 at the proximal end of the shaft 36. As shown in FIG. 7, the cam surface 50 includes a loading region 51 separated by a hump 52 from an operating region 53.

Figure 11:
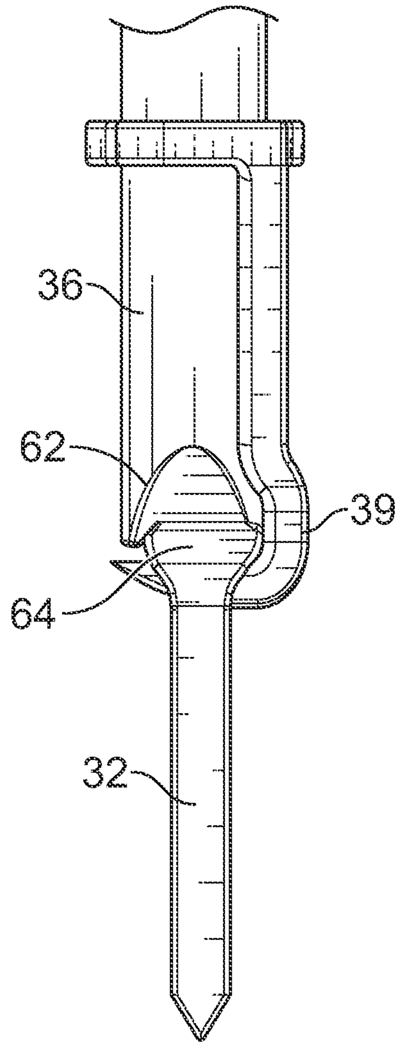
FIG. 11 is a relatively enlarged side elevation of a portion of the distal end of the staple instrument and loaded staple shown in FIG. 9, illustrating the distal end of the shaft.

As seen variously in FIGS. 8-11, jaws 38, 39 support the staple 32. When the staple 32 is in a loaded position, as seen in FIG. 11 the distal end 62 of the shaft 36 cooperates with the jaws (one jaw 39 shown in FIG. 11) to retain the staple 32. The distal end 62 of the shaft 36 has a terminal contour that cooperates with the bridge 64 of the staple 32 to retain the staple in the intended position and to inhibit movement of the staple during actuation of the instrument, as best seen in FIG. 11. The position shown in FIG. 11 is the normal load position of the staple and is the position in which the staple instrument could be supplied to a user. Notably, the staple instrument is capable of holding a pre-loaded staple with the jaws each maintained at an angle of less than 90° with respect to a horizontal axis of the bridge of the staple, this axis being parallel to a line drawn to connect the tips of the jaws. The staple may be held for example with each such jaw angle ranging from 80° to less than 90°. This angle can be, for example, 81°, 82°, 83°, 84°, 85°, 86°, 87°, 88°, or 89°.

Also, as seen in FIGS. 3 and 4, the staple instrument 34 includes a spring 55 that engages the housing at a distal end 58 of shaft channel 60. The spring engages a radially enlarged portion 67 (FIG. 4) of the shaft 46 and normally biases the shaft 36 in a proximal direction relative to the housing 40. Because the spring 55 biases the shaft 36 in a proximal direction, the cam driver 48 continuously engages the cam surface 50. The cam surface 50 and cam driver 48 thereby define a coupling mechanism that converts rotation of the handle into axial translation of the shaft. Ears 54, 56 (FIGS. 4 and 7) cooperate with internal guide channels defined by respective slot segments 57, 59 (FIGS. 5 and 6) to prevent relative rotation of the shaft 36 and housing 40.

Figure 12:
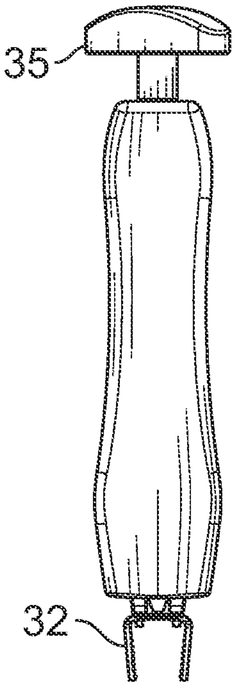
FIG. 12 is a front elevation of the staple instrument and a staple in a pre-load position.
Figure 12A:
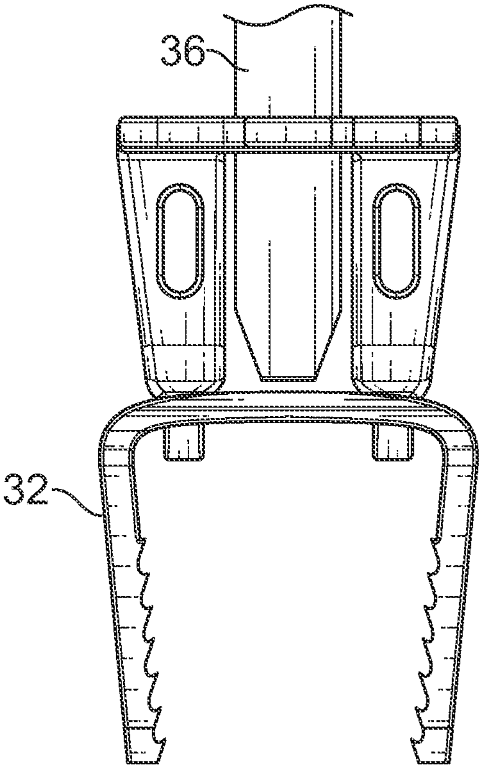
FIG. 12A is a relatively enlarged front elevation of the distal end of shaft and staple holder when in the pre-load position.
Figure 13:
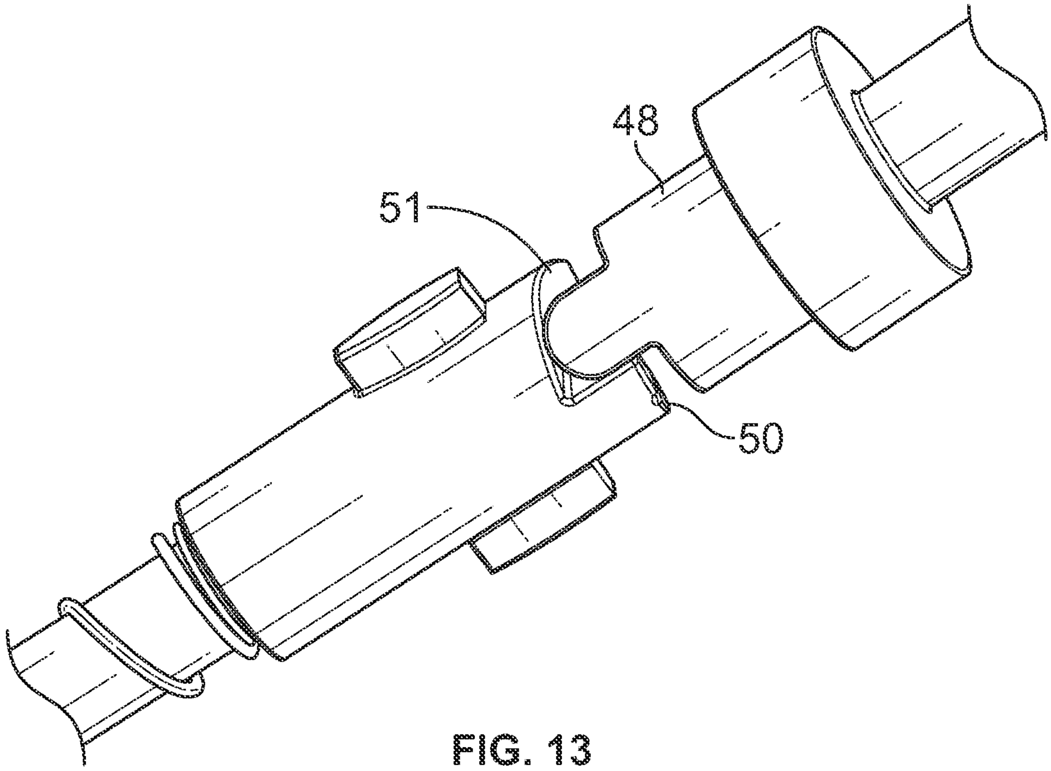
FIG. 13 is a relatively enlarged perspective view illustrating engagement of the cam driver portion of the handle of the staple instrument with the cam surface of the proximal end of the shaft, the staple instrument being positioned in the pre-load position as shown in FIG. 12.
Figure 14:
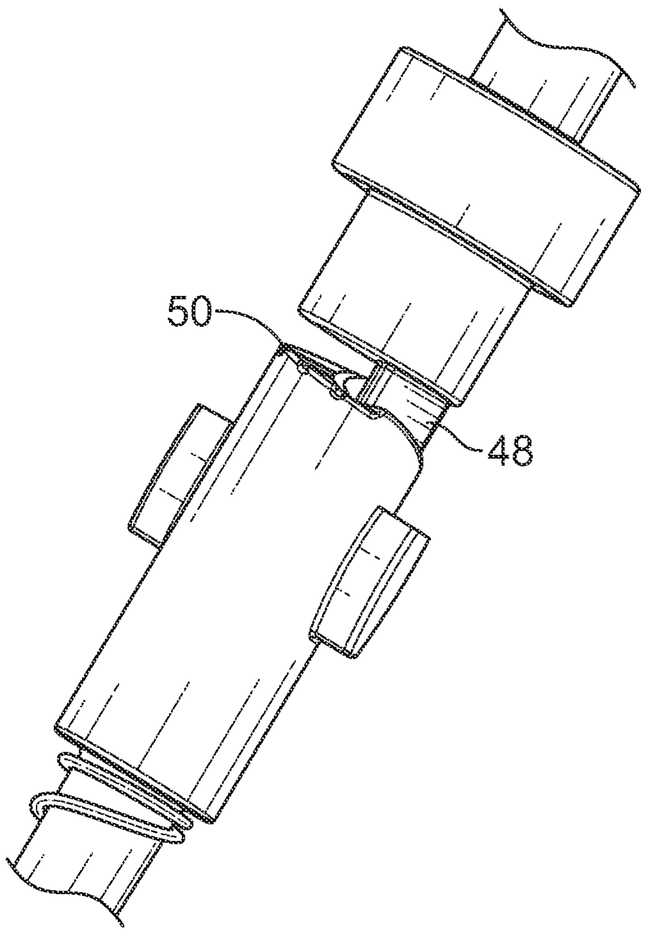
FIG. 14 is a second perspective view of the components shown in FIG. 12 as seen from a different perspective.

Operation of the device is seen with respect to the staple instrument 31 as illustrated in FIGS. 12-18. When it is desired to place a staple onto the staple instrument, whether during preparation of the kit or by the operator, the handle 35 is turned to its most counterclockwise position such that the shaft is fully retracted as seen in FIG. 12. In this position, the cam driver 48 is positioned at the loading region 51 of the cam surface 50, as seen in FIGS. 13 and 14. The staple 32 is unstressed and unstrained in this position, disregarding de minimis stress and strain caused by contact of the staple with the jaws. As seen in FIG. 12A, the shaft 36 does not contact the staple 32 in this position and the legs of the staple 32 are in their normal unbiased resting position.

Figure 15:
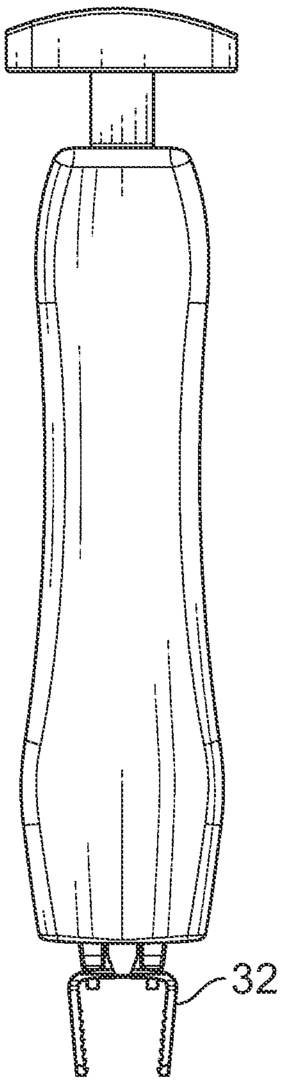
FIG. 15 is a front elevation of the staple instrument shown in a staple loaded position.
Figure 15A:
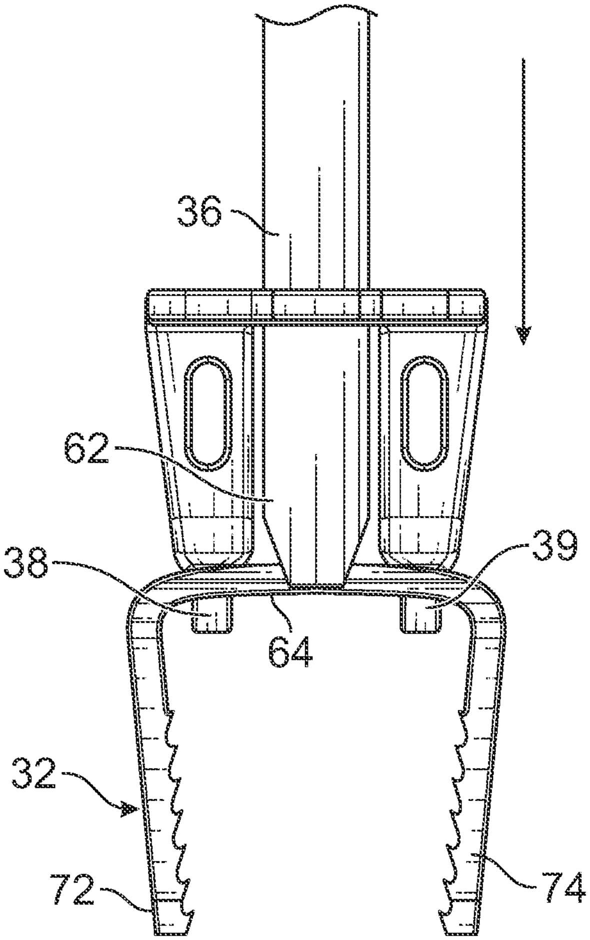
FIG. 15A is a relatively enlarged front elevation of the distal end of the shaft and staple holder when in the staple loaded position.
Figure 16:
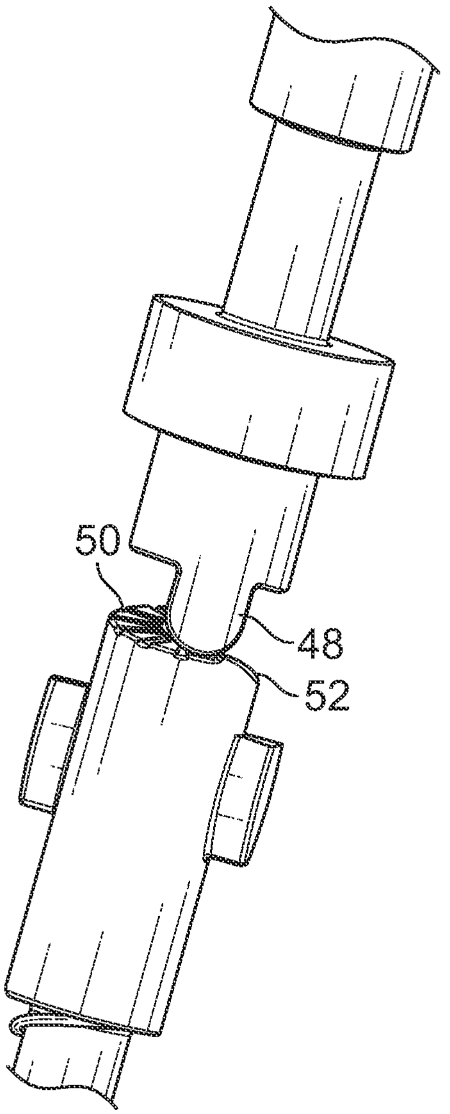
FIG. 16 is a relatively enlarged perspective view illustrating the engagement of the cam driver and cam surface of the staple instrument shown in the staple loaded position illustrated in FIG. 15.

Clockwise rotation of the handle causes the cam driver 48 to move relative the cam surface 50 to thereby bias the shaft 36 in a relatively distal direction. The shaft is constrained by the ears 54, 56 and guide channels 57, 59 to axial translation, and the shaft cannot rotate with respect to the housing, disregarding de minimis movement allowed by part tolerances. Upon such advancement of the shaft to the staple loaded position shown in FIG. 15, the cam driver 48 first traverses the hump 52, as seen in FIG. 16. This provides an audible and tactile indication to the assembler or operator that the staple is now in the staple loaded position. As best seen in FIG. 15A, in this position the distal end 62 of the shaft cooperates with the jaws 38, 39 to create a three-point bending moment on the staple 32, with the shaft 36 engaging the bridge 64 of the staple 32 at a position between the positions at which the jaws 38, 39 engage the bridge 64. The bridge 64 of the staple is thereby strained to cause the legs 72, 74 of the staple to open and to separate.

Figure 17:
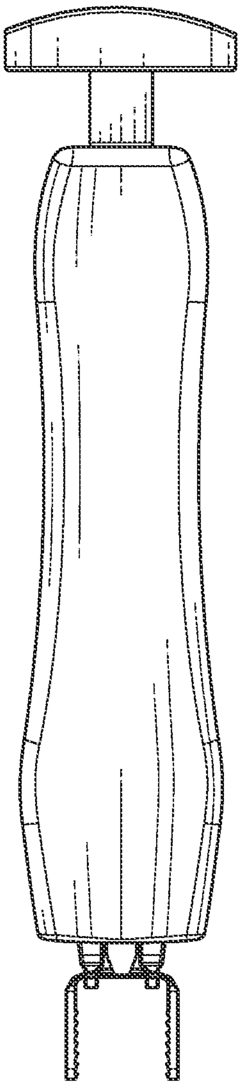
FIG. 17 is a front elevation of the staple instrument shown in a staple insertion position.
Figure 17A:
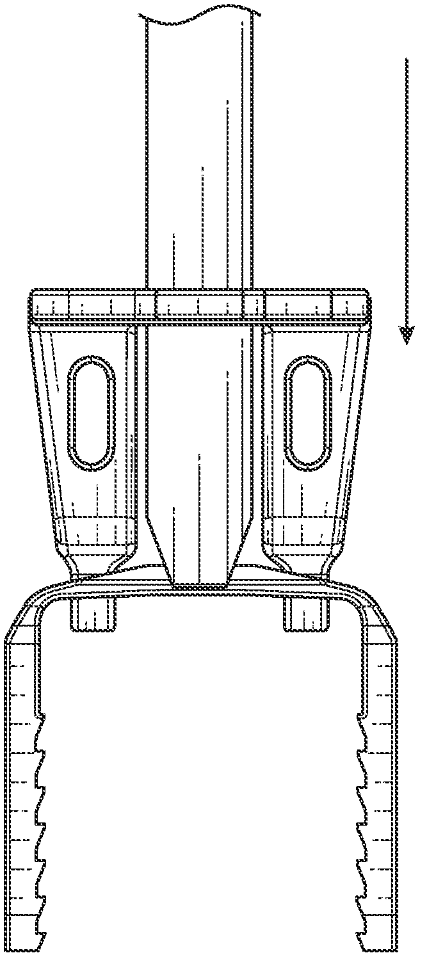
FIG. 17A is a front elevation of the staple instrument shown in the staple insertion position.
Figure 18:
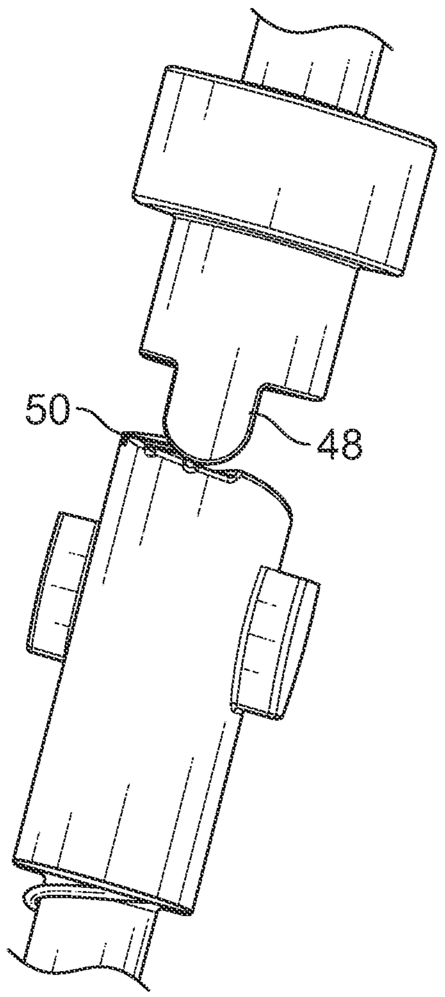
FIG. 18 is a relatively enlarged perspective view illustrating the engagement of the cam driver and cam surface of the staple instrument shown in the staple insertion position as illustrated in FIG. 17.

Typically, the staple is placed in pre-drilled holes in a bone or in bone segments of a patient. When it is desired to so insert the staple, the operator then continues to turn the handle 35 clockwise to continue to advance the shaft 36. The cam surface 50 is provided with a plurality of troughs 70 (FIG. 7). The troughs 70 provide further audible and tactile feedback to the operator as the handle 35 is rotated. Additionally, the troughs 70 retain the tip of the cam driver 48 therewithin to inhibit counterrotation. As the handle is rotated, the cam driver 48 continues to traverse the cam surface 50 to advance the shaft further and to further strain the bridge of the staple. As seen in FIGS. 17 and 17A, the legs of the staple are approximately parallel to one another, thereby allowing the operator to place the staple into parallel bone bores. As seen in FIG. 18, the cam drive 48 has advanced to the position shown along the cam surface 50.

When the staple has been placed into this position, the operator may rotate the handle counterclockwise to retract the shaft and thereby allow separation of the staple 32 from the jaws 38, 39 of the staple instrument.

The staple instrument may be operated in some cases to remove staples by operating the device in a reverse sequence from that described above.

The staple is typically made of titanium, a titanium alloy, or another biocompatible material. The other components may be made of stainless steel. In some embodiments of the housing, shaft, and handle may be made of ABS or another suitable plastic material. The components may be manufactured and assembled using conventional techniques. The staple instrument may be a durable, reusable device, or it may be a single-use device when packaged with or sold in conjunction with one or more staples. If intended for durability, the components are preferably all composed of metal that is capable of withstanding a sterilization procedure.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A staple instrument comprising a staple holder comprising a pair of jaws;

a drive shaft;

a rotational handle;

a coupling to convert rotational motion of the handle into axial advancement of the shaft;

a distal end of the shaft positioned to cooperate with the jaws of the staple holder for causing three-point bending of a staple bridge;

said coupling including a cam surface cooperating with a cam driver.

2. A staple instrument according to claim 1, the cam surface being disposed on a proximal end of the shaft and the cam driver being disposed on a distal handle end.

3. A staple instrument according to claim 2, the cam surface including a loading region separated by a hump from an operating region.

4. A kit comprising the staple instrument of claim 1 and a staple.

5. The kit of claim 4, said staple instrument and said staple being disposed within a container.

6. The kit of claim 4, a distal end of the shaft having a contoured end shaped to retain a bridge of the staple.

7. The kit of claim 4, the staple being loaded on said staple holder with each jaw angle ranging from 80° to less than 90°.

* * * * *